(12) United States Patent
Trogolo et al.

(10) Patent No.: US 8,518,449 B2
(45) Date of Patent: *Aug. 27, 2013

(54) POLYMER PARTICLE COATING METHOD

(75) Inventors: Jeffrey A. Trogolo, Boston, MA (US); Edward K. Welch, II, Naples, FL (US)

(73) Assignee: Sciessent LLC, Wakefield, MA (US)

( * ) Notice: Subject to any disclaimer, the term of this patent is extended or adjusted under 35 U.S.C. 154(b) by 202 days.

This patent is subject to a terminal disclaimer.

(21) Appl. No.: 11/895,329

(22) Filed: Aug. 24, 2007

(65) Prior Publication Data

US 2008/0047894 A1   Feb. 28, 2008

Related U.S. Application Data

(60) Provisional application No. 60/840,287, filed on Aug. 25, 2006.

(51) Int. Cl.
*A61K 9/50*   (2006.01)
*C08J 3/02*   (2006.01)
*C08K 3/20*   (2006.01)

(52) U.S. Cl.
USPC .......................................... 424/497; 524/457

(58) Field of Classification Search
None
See application file for complete search history.

(56) References Cited

U.S. PATENT DOCUMENTS

| 4,092,460 | A | * | 5/1978 | Cerny et al. .................. 428/407 |
| 4,608,247 | A | | 8/1986 | Heinig, Jr. |
| 4,629,645 | A | | 12/1986 | Inoue |
| 4,663,359 | A | | 5/1987 | Rei |
| 4,861,489 | A | | 8/1989 | Swift et al. |
| 5,180,585 | A | | 1/1993 | Jacobson et al. |
| 5,187,220 | A | * | 2/1993 | Richart et al. ................ 524/441 |
| 5,238,749 | A | | 8/1993 | Cueman et al. |
| 5,603,987 | A | | 2/1997 | Lisenko |
| 5,639,550 | A | | 6/1997 | Lisenko |
| 5,980,620 | A | | 11/1999 | Brodie et al. |
| 6,093,407 | A | | 7/2000 | Cummings et al. |
| 6,113,979 | A | | 9/2000 | Sagawa et al. |
| 6,129,782 | A | | 10/2000 | Brodie et al. |
| 6,432,416 | B1 | | 8/2002 | Cummings et al. |
| 6,514,413 | B2 | | 2/2003 | Pimenov et al. |
| 6,524,477 | B1 | | 2/2003 | Hughes |
| 6,540,916 | B2 | | 4/2003 | Patil |
| 6,551,608 | B2 | | 4/2003 | Yao |
| 6,613,703 | B1 | * | 9/2003 | Yahiaoui et al. ................ 442/76 |
| 2003/0096017 | A1 | | 5/2003 | Decker et al. |
| 2003/0141620 | A1 | | 7/2003 | Stevenson et al. |
| 2004/0180098 | A1 | | 9/2004 | Decker et al. |

FOREIGN PATENT DOCUMENTS

| GB | 2297552 | 8/1996 |
| JP | 63239205 | 10/1988 |
| JP | 8060036 | 3/1996 |
| JP | 08199089 A2 | 8/1996 |
| JP | 08217998 A2 | 8/1996 |
| JP | 8239598 | 9/1996 |
| JP | 9263715 | 10/1997 |
| JP | 10168346 | 6/1998 |
| JP | 10316899 A2 | 12/1998 |
| JP | 2000-290114 | 10/2000 |
| WO | WO94/11446 | 5/1994 |
| WO | WO97/46626 | 12/1997 |
| WO | WO98/13429 | 4/1998 |
| WO | WO99/18162 | 4/1999 |

* cited by examiner

*Primary Examiner* — Carlos Azpuru
(74) *Attorney, Agent, or Firm* — Edward K. Welch, II; IP&L Solutions (57) ABSTRACT

An improved method for fixedly binding particles of a solid, heat absorbing material or additive, especially polymer additives, to the surface of prepolymer and/or polymer particles.

13 Claims, 1 Drawing Sheet

POLYMER PARTICLE COATING METHOD

1. RELATED APPLICATION

This patent application claims the benefit of previously filed U.S. Provisional Patent Application No. 60/840,287 entitled "Polymer Particle Coating Method" filed on Aug. 25, 2006, which is hereby incorporated herein in its entirety by reference.

2. TECHNICAL FIELD

The present invention is directed to an improved method of fixedly coating particles of prepolymers and/or polymers with microparticles of a solid, heat absorbing material. In particular, the present invention is directed to an improved method of preparing antimicrobial prepolymer and/or polymer granules and powders, especially prepolymer and polymer granules and powders used in water filtration media, polymer masterbatch and compression molding applications. The improved method involves individually heating the prepolymer and/or polymer particles and the microparticles of the solid material to temperatures whereby when the two are brought into intimate contact with one another, they will fuse to each other, but not to themselves.

3. BACKGROUND

The addition of solid additives to a polymer material is typically accomplished by dry blending or dry mixing or by direct incorporation, particularly solution or melt blending. The method chosen depends upon a number of factors including the relative size of the additive particle to the polymer particles, the sensitivity of the additive material to the process steps by which the addition is to be attained as well as to the materials used, and the desired property or objective of the additive itself. Each method has its attributes and its problems or issues: none is ideal for all circumstances.

Dry blending is perhaps the most simplest and cost effective means of producing a binary system of two solid particle materials. The polymer particles and the solid additive particles are merely placed in a vessel and the vessel rotated, like a cement mixer, to intimately mix the two and/or a mixer means is incorporated or inserted into the vessel to mix the components. This process is especially suited for mixing polymer particles and additive particles of approximately the same size and mass. Because of their similar size, once the distribution is established, the distribution will remain fairly stable, regardless of shaking or vibrations. On the other hand, when the additive particles are of disparate size, especially where the sizes are orders of magnitude in difference, it may be impossible to achieve a truly stable, homogeneous distribution as the smaller particles will continually cascade down through and settle from the larger particles during the mixing process. Thereafter, the cascading will tend to continue as the mixture is moved, shaken or otherwise subjected to vibrations and the like.

Nonetheless, where the particle size difference is marked and the quantities of the additive are not overly excessive, one may achieve a fairly uniform coating of the polymer particles with the additive particles, much like the addition of powdered cinnamon to granular sugar. However, the adherence of the one to the other is typically reliant upon Van Der Waals forces and/or electrostatic charges, both of which are relatively low in strength. In the absence thereof, and even in the presence thereof due to the inherent weakness of such forces and charges, dissociation and settling occurs, particularly during handling and transport of thereof. Thus, without proper remixing of the composition prior to use, portions thereof will have little or no additive while others will have excessively high levels of the additive. For example, in molding applications, articles made with materials taken from the top of the storage container will have higher loadings of the additive than those made from materials taken from the bottom of the storage container.

Depending upon the intended processing and/or end-use of these materials, even with proper remixing, the additive materials may readily dissociate from the surface of the polymer particles due to shock, vibration or shaking in subsequent processing steps, application steps or use. Similarly, if the materials are to be used in a flow environment, the force of the flow stream, whether a gas, such as air; a liquid such as water, or even a flowable solid, will tend to strip the additive particles from the surface of the polymer particles. For example, the process of loading a sample of the mixture into a hopper and subsequently a compression molding machine may subject the coated particles to sufficient shock that the additive particles dissociate from the polymer particles and settle to the bottom of the hopper or compression molding machine. In the former, parts made from materials taken from the top of the hopper will have less or a lower concentration of the additive than those taken from the bottom. Similarly, in the latter, the bottom surface of the compression molded part will tend to have a higher concentration of the additive than the upper surface. In flow environments, for example in water treatment applications where polymer media is coated with various additives such as sequestering agents, antimicrobial agents, and the like, the water flow through the media, as well as shocks and vibrations upon the media vessel, may result in the dissociation of the additive and; consequently, the loss of the additive particles into the flow stream and the concurrent loss of efficacy/performance.

While dry mixing may be the simplest and least costly method of preparing such combinations, the most common is perhaps melt blending. Melt blending typically involves adding the additive particles and the polymer particles individually or as an intimate, dry mixture to an extruder whereby the additive is intimately incorporated into the polymer as it melts and proceeds through the extruder. Alternatively, the solid additive particles may be added to the polymer melt already in an extruder barrel through a second port further down the screw or barrel of the extruder. In both instances, the melt readily entombs the additive particles; however, oftentimes the additive, particularly when in powdered form, especially as a fine powder, is poorly dispersed in the polymer melt due to agglomeration thereof during the incorporation process and/or poor wetting. While relative particle size of the additive to the polymer material is not so much of a concern here since the additive is added to a melt of the polymer, the smaller the additive particle size, the greater the concern with poor wetting and dispersability. On the other hand, as the additive particle size increases, there is concern for wear and interference with the operation of the extruder and subsequent pelletizing equipment. Regardless, as a result of poor wetting and/or dispersability, the physical or performance properties associated with the presence of the additive may not manifest or may manifest in a non-uniform manner. Furthermore, such agglomeration may cause the appearance of physical imperfections in parts and articles made, directly or indirectly, from the melt, especially in the case of transparent or translucent materials and those used in forming films.

Typically, the foregoing concerns can be avoided or at least lessened by the preparation of concentrates or, as they are oftentimes referred to, masterbatches or pre-mixes wherein large amounts of the additive are combined, typically through melt blending, with the same or a different, more accommodating polymer and pelletized and those pellets subsequently sold for use in combination with, or directly combined with, virgin pellets of the ultimate polymer in a second extrusion process. In essence, the high additive concentration masterbatch is "let down" though a subsequent extrusion blending process. The product of the "let down" process is then pelletized for commercial sale of a final polymer composition or directly injected or extruded into various extrusion or molding equipment for manufacture of the end product(s)/article(s) or manufacture. Here, however, concerns arise with respect to compatibility of the masterbatch polymer with the ultimate polymer, if different, and, perhaps more importantly, with the sensitivity of the masterbatch polymer and/or additive to the repetitive high temperature extrusion cycles. The latter is especially of potential concern for organic and metalorganic additives, which, as opposed to most inorganic additives, tend to be much more heat sensitive. Such high temperatures may adversely affect the physical as well as performance characteristics of the additive or, in the case of heat activated additives, cause the premature activation thereof.

Solution blending overcomes many of these issues; yet introduces another set of issues altogether. Since most polymers are not water soluble, one must employ various organic solvents or co-solvents. Besides adding materials costs, the use of solvents, especially organic solvents, creates a number of additional concerns relative to environmental, health and safety precautions, most especially for capturing the solvent as it is evaporated to recover the polymer material. Furthermore, the additives themselves may be sensitive to or adversely affected by the solvents and recovery processes.

An additional pitfall of the aforementioned incorporation methods is the fact that certain additives are intended only for providing surface characteristics and/or are effective only if at the surface of the polymer particle or, in the case of articles of manufacture made thereof, the substrate surface of the so manufactured product. For example, glitter (small metal or metallic appearing flakes) on the surface of the polymer particle or article of manufacture will manifest its reflective/glittery appearance; however, that within the body or matrix of the polymer will not. Similarly, antimicrobial agents must either be present on the substrate surface or migrate through the polymer matrix to the substrate surface to be effective in providing antimicrobial performance. In the absence of the ability to migrate, that portion of the antimicrobial agent within the polymer matrix is unavailable to provide antimicrobial efficacy. This is especially of concern for inorganic antimicrobial agents, especially those that rely upon an ion-exchange type mechanism for performance. As a consequence, direct incorporation requires the use of much higher levels of the antimicrobial agent in order to achieve even a reasonable, though oftentimes short-lived, antimicrobial performance. Such higher loadings may adversely affect the physical properties of the polymer into which they are incorporated and add costs, a key consideration with, for example, ion-exchange type antimicrobial agents which tend to be fairly expensive. While dry blending to surface coat the polymer particles may overcome this concern, it introduces the problems previously mentioned above.

One method of addressing, at least in part, the aforementioned problems and pitfalls of direct incorporation and, where appropriate, dry blending is through the use of elevated temperatures in the dry blending process. Specifically, the dry blend is mixed at high speed and/or with direct elevation of temperature in the mixing vessel so as to elevate the mixture to a temperature at or above the melt temperature of the polymer or at least to that temperature at which the polymer becomes tacky. At this elevated temperature, the particles of polymer and additive become adhesively bonded to one another. This process may cause a deformation of the polymer particles, which may be detrimental for certain applications such as water treatment applications or powder coating applications. More significantly, this process causes an agglomeration and fusing of the polymer particles to themselves. Consequently, the product of this process must be screened in order to separate out the agglomerated particles which are then subjected to a further grinding operation to break apart the agglomerations. Depending upon the ultimate use of the treated particles, most often the reground particles must be re-entered into the coating process to ensure that those areas where another polymer particle had previously bonded are now coated with the additive materials. Besides the concerns with agglomeration, this coating process requires the use of specialized, especially coated equipment and strict/careful process controls, especially temperature controls, to ensure that the molten or tacky polymer particles do not adhere and bind to the mixing vessel, the mixing equipment or any other conduit or transport equipment before they are adequately cooled so as to no longer exhibit tacky or adhesive characteristics or, worse, to prevent the whole mass from fusing or congealing in the mixer vessel and the attendant consequences thereof.

Alternatively, the art has also suggested solution bonding and/or coating compositions as means to impregnate or coat the prepolymer or polymer particles with the additive: thereby, physically bonding the additive to the surface of the polymer particle. However, as mentioned above with respect to solution blending, these methods introduce new material(s) to the overall composition and/or employ material(s) that may raise environmental, health and safety issues as well as issues relative to the performance of the additives and/or the resultant polymer compositions themselves. Furthermore, these methods entail additional and oftentimes complex or costly processing steps and the attendant capital equipment needs as well as longer processing times. For example, solution impregnation is only commercially feasible for those solvents that are not overly toxic, expensive, difficult to handle, etc. and is limited to those prepolymer and polymer compositions that swell in the given solvent as well as those additives that are soluble in or easily suspended in the chosen solvent. Furthermore, one must employ appropriate means to contain and recover the solvents. Similarly, besides the introduction of the new materials and the costs associated therewith, coating processes require specialized coating apparatus and processes to ensure that the polymer particles are individually coated without, or without significant, agglomeration of the coated polymer particles. Consequently, neither is a truly viable, economical option.

Thus, there remains a need for a method of combining solid additives and polymer particles wherein the mixture remains stable, particularly in the case of marked particle size differences and irrespective of whether the combined materials are subject to vibration or shock or flow.

There also remains a need for a method of fixedly combining solid additives and polymer particles without directly incorporating the additive into the polymer.

Further, there remains a need for combining solid additives and polymer particles without the use of solvents and without the need for highly specialized and expensive equipment.

Finally, there remains a need for a method of fixedly combining solid additives and polymer particles which method is simple and does not result in any significant agglomeration and/or fusing of the polymer particles. In particular, there remains a need for a simple process for successfully binding an antimicrobial powder to the surface of prepolymer and polymer particles which avoids the use of additional chemical agents and additives, avoids concerns of agglomeration of the prepolymer and/or polymer particles, does not require the purchase and implementation of expensive/additional equipment, and can be accomplished at low cost.

4. SUMMARY

In accordance with the present invention there is provided an improved method of fixedly coating particles of prepolymers and/or polymers with particles, especially microparticles, of a solid, heat absorbing material or additive, especially polymer additives. In particular, there is provided an improved method wherein a) the prepolymer and/or polymer particles are heated to a temperature below that at which the surface of the particles begins to become tacky or manifest adherent properties and b) the microparticles of the solid, heat absorbing materials are heated to a temperature at or, preferably, above the temperature at which the prepolymer or polymer becomes tacky or begins to manifest adherent properties, and c) allowing the additive material microparticles to become fixed to the surface of the prepolymer or polymer particles. Preferably, the prepolymer and polymer particles are heated to at least their Vicat temperature while the solid, heat absorbing microparticles are heated to a temperature of at least 10° C., preferably at least 20° C., most preferably at least 50° C., above the temperature at which the prepolymer or polymer becomes tacky or begins to manifest adherent properties.

The process of the present invention is practiced in several ways. In one embodiment, particles of the additive material and the prepolymer or polymer particles are heated in separate vessels and, subsequently, intimately mixed so as to allow the former to coat and become fixed to the surface of the latter. Mixing may be performed in a third vessel or, should the apparatus allow, the heated particles of one vessel may be added to those of the second vessel. In an alternate embodiment, the particles of the additive material and the prepolymer and/or polymer particles are intimately mixed prior to and/or concurrent with exposure to conditions which preferentially or selectively heat the former whereby the former are elevated to the desired temperature while the latter are only elevated to a temperature below that at which the surface of the particles begins to become tacky or manifest adherent properties.

The process of the present invention is applicable to the bonding of most any solid, heat absorbing additive material, particularly polymer additive materials, to a polymer or prepolymer particle. For many solid additives the present invention provides an alternative to the process of melt blending/-compounding or solution blending/coating as a means to integrate said additives into the prepolymer and/or polymer material. However, for those additives which are sensitive to the compounding conditions or to solvent type applications or which may undesirably affect the prepolymer or polymer matrix or the performance of the additive during or subsequent to its incorporation into the polymer particle, it offers an improved and beneficial method or, in certain instances, the only means to effectively incorporate or combine the additive with the polymer particle, other than dry blending.

The process of the present invention is especially suited for and provides a benefit relative to the formation of polymer masterbatches and pre-mixes, water treatment media, powder coatings, compression molding compositions and agricultural agents. Most especially, the present invention is suited for fixedly binding decorative and/or functional additives to the surface of polymer particles for use in products and applications where it is disadvantageous, economically and/or functionally, to have the additive dispersed throughout the polymer matrix. For example, as noted above, it is disadvantageous to incorporate inorganic antimicrobial agents that rely upon a release of the antimicrobial active agent for providing bioefficacy into a polymer whereby the release is impeded or prohibited. The same holds true for various agricultural chemicals such as fungicide actives, herbicide actives, and the like.

6. DETAILED DESCRIPTION

For purposes of clarification, the temperature at which the prepolymer or polymer "begins to manifest adherent properties" is that temperature at which the prepolymer or polymer begins to exhibit tack and is evidenced by the onset of agglomeration of the prepolymer or polymer particles: though it is recognized that the agglomeration, at this point, is minimal and readily broken with the application of light or minimal pressure such as simple touching or rolling the materials between one's fingers. This temperature may be, but is typically less than the glass transition temperature (Tg) in the case of amorphous materials and the melt temperature in the case of crystalline materials. Further, unless otherwise stated herein, as used herein and in the appended claims the phrase "begins to manifest adherent properties" is also intended to include and reference physical entrapment: the latter referring to those circumstances where the prepolymer and/or polymer particles are heated to its Vicat temperature or to a temperature within about 5° C. (above or below) its Vicat temperature and the additive particles are heated to a temperature sufficiently higher than that of the prepolymer or polymer particles so that when the two are in forced contact with one another, the heat of the additive particles further softens the prepolymer or polymer material at the interface and becomes embedded therein, with or without an adhesive bond being formed, i.e., the heat of the additive particles may not be sufficient to actually melt the polymer at the interface of the additive particle and prepolymer or polymer particle so as to form the adhesive bond. The forced contact may result from physical mixing or merely the compression experienced due to the weight of the mixture. Typically, the additive particles will be heated to a temperature that is at least about 10° C. higher, preferably at least about 20° C. higher, most preferably at least about 50° C. higher, than that of the prepolymer or polymer particles and is at least about 10° C., preferably at least 20° C., most preferably at least 50° C., above the Vicat temperature of the prepolymer and/or polymer particles. For the present invention, the Vicat temperature, more commonly known as the Vicat softening temperature, is determined according to ISO 306 (ASTM D1525) using method is B50.

Additionally, unless contrary or contradictory to the context in which they are used, it is to be understood that the terms "polymer particles", "prepolymer particles" and "prepolymer and/or polymer particles" are used interchangeably herein and in the appended claims. In following, as noted below, the polymers may be thermoplastic or thermoset: though the invention is especially suited for use with thermoplastic polymers. Said polymer and prepolymer particles may be in the form of powders, granules, pellets, chopped fibers, and the like. Further, except as otherwise stated herein, reference herein to a particle size or particle size range means that at least 60%, preferably at least 80% and most preferably at least 95% of the particles meet the particular limitations. Where particle size uniformity is important, at least 60%, preferably at least 80%, of the powder coating particles will fall within 20 microns, most preferably, 10 microns, of the specified average particle size. Finally, for the sake of simplicity, it is hereby affirmed that all patents and patent applications mentioned herein, specifically their teachings, are hereby incorporated herein, in their entirety, by reference.

In its broadest concept, the present invention provides an improved process for binding solid, heat absorbing materials or additives to polymer or prepolymer particles. In particular, the process relates to the binding of solid micro- and nano-sized particles to micro- and macro-polymer particles. Although the process may be employed for bonding most any solid additive material to the polymer and/or prepolymer particles, it is especially suited for use in those circumstances where it is not desirable or not feasible to directly incorporate the solid additive into the polymer matrix concurrent with or prior to the intended end-use of the polymer composition with which it is to be associated.

Generally speaking, the process of the present invention comprises heating a) the prepolymer and/or polymer particles to a temperature below that at which the surface of the particles begins to become tacky or manifest adherent properties and b) the particles of the solid, heat absorbing additive material to a temperature at or above the temperature at which the prepolymer or polymer becomes tacky or begins to manifest adherent properties and allowing the additive material particles to become fixed to the surface of the prepolymer and polymer particles. As discussed in greater detail further below, the process may be practiced in several ways. In one embodiment, the additive material particles and the prepolymer and/or polymer particles are heated in separate vessels and, subsequently, intimately mixed so as to allow the former to coat and become fixed to the surface of the latter. Mixing may be performed in a third vessel or, should the apparatus allow, the heated particles of one vessel may be added to those of the second vessel. In an alternate embodiment, the additive material particles and the prepolymer and/or polymer particles are intimately mixed prior to and/or concurrent with exposure to conditions which preferentially or selectively heat the former whereby the former are elevated to the desired temperature while the latter are only elevated to a temperature below that at which the surface of the particles begins to become tacky or manifest adherent properties.

In one embodiment of the present invention the method is employed for preparing polymer premixes or master-batches for molding and/or extrusion applications. Premixes typically comprise a polymer carrier and one or more polymer additives, generally as a powder, and, as mentioned above, are employed as an efficient and simplified means of delivering and incorporating polymer additives, especially colorants and other finely powdered additive materials, into a polymer melt. Although premixes typically have the additive homogeneously mixed throughout the polymer particle, such may not be desired where the additive is co-reactive with a component, by-product or contaminant of the polymer and/or where the additive affects the melt flow or viscosity characteristics of the polymer into which it is incorporated. In the former, reactivity is limited to the interface between the polymer particle and the solid particle or may be non-existent if the reactivity is heat sensitive and the temperature needed to initiate the reaction is higher than that needed to effect the present invention. In the latter, an increase in viscosity or decrease in melt flow may affect the ease and/or completeness with which the premix polymer is incorporated into the neat resin. By adhering the viscosity modifier to the surface of the premix particle, the viscosity effect occurs during the melt blending of the carrier polymer and neat resin.

In a second embodiment of the present invention, the process is employed in making macro-sized polymer particles which are themselves employed in making molded parts by fusion bonding or compression molding. Here the treated polymer particles are placed into a form and fused through heat and pressure. Since very little flow occurs during the molding process, a high concentration of the solid additive remains at the surface resulting in a more efficient use of the same. This aspect of the present invention is especially directed towards the incorporation of decorative and/or functional additives which only function or provide their benefit at the substrate surface. Exemplary additives to which this aspect of the present invention is applicable include, but are not limited to, purely decorative additives like glitter or other reflective materials; conductive metals in powder, flake or fiber form for providing EMI/RFI shielding or for dissipating electrostatic charges that may otherwise build up in or on or be transferred to the coated article and antimicrobial agents which do not bloom or have transport mechanisms through the chosen polymer matrix, especially in articles employed in industrial, commercial and consumer food preparation and service, e.g., ultrahigh molecular weight PE (UHMWPE) cutting boards and work surfaces. Each of these benefit economically and performance-wise from the high concentration of the additive at the substrate surface.

In a third embodiment of the present invention, the process is employed in making polymer particles for use in water filter media. Here the polymer particles are used as carriers for introducing or incorporating certain functional materials into filter media. For example, they may be used to incorporate sequestering agents, especially heavy metal sequestering agents, or antimicrobial agents into filter media. The process of the present invention allows one to provide a high concentration of the additive at the surface of the polymer particle without concern that it will be washed away by water flow or settle out due to impact, shock or vibrations to the filter elements. These particles may be employed in a loose fill or sintered form and are preferably used in conjunction with other particulate filter media components, especially such granular activated carbon (GAC).

In a fourth embodiment of the present invention, the process is employed in making dispersible bioactive agricultural and/or horticultural products. Many bioactive agents for use in agriculture and horticulture are fine powders. Although many can be dispersed or suspended in water or another liquid medium for application, others are preferentially applied as a "dust." One of the problems with dust is the carry of the dust particles away from the intended target. Adding the bioactive to a solid carrier increases its bulk and, thus, provides better control for its application. Thus, in accordance with this embodiment of the invention, fungicides, herbicides, insecticides and the like may be adhered to the surface of polymer particles for application. And, since all or essentially all of the bioactive component is on the surface of the polymer particle, it is available for providing its intended bioefficacy.

Finally, as discussed in copending U.S. patent application entitled "Antimicrobial Powder Coatings and Method" in the name of Jeffrey A. Trogolo et. al., filed concurrently with this application (and claiming priority from Provisional Patent Application No. 60/840,286, filed Aug. 31, 2006), which is hereby incorporated herein in its entirety, the process of the present invention is especially and surprisingly beneficial for use in the preparation of powder coating compositions, both thermoset and thermoplastic, wherein it is desired that the finished powder coating have a high concentration of a solid additive at its surface. For example, as discussed above with respect to compression molding compositions, it may be desirable or necessary to have a high concentration of a decorative or functional additive, such as glitter, conductive materials or antimicrobial agents, at the surface of the formed powder coating on a given substrate to which it has been applied.

The process of the present invention is applicable for both thermoplastic and thermosetting polymer or prepolymer materials or compositions in particle form; though, it is especially suited for use with thermoplastic polymer particles. Exemplary thermosetting materials include those comprising curable or cross-linkable unsaturated polyester resins, epoxy resins, acrylic resins, phenol resins, melamine resins, urea resins urethane resins, vinyl ether resins, etc., as well as combinations of such resins or resins have a combination of such functional groups, including epoxy-polyester resins, acrylourethane resins, and the like. For thermosetting molding and powder coating compositions, the heat retentive solid additive, e.g., the antimicrobial agent, may be applied to particles of the neat thermosetting resin or to premix particles which comprise the thermosetting resin along with other typical ingredients of the powder coating including hardener or curing/cross-linking agent, colorants, stabilizers, fluidity agents, dispersants, antifoaming agents, thickeners, etc.; though the hardener or curing or cross-linking agent may be a separate additive to the thermosetting powder coating composition. Such thermosetting powder coatings may cure or set through chemical reaction with a hardener or the like or cure or cross-linking may be induced by heat, actinic radiation (especially UV exposure), and the like.

As noted, the present invention is most especially suited for use with and of benefit to thermoplastic polymer particles due to the diversity of end-use applications and the ease of use therewith. Suitable thermoplastic polymer particles that may be used in accordance with the practice of the present invention include polyamides such as nylon 6, nylon 6,6, nylon 6,121; acrylics such as polymethylmethacrylate; polyolefins such as polyethylene, LLDPE, UHMWPE, and polypropylene; polyvinyl alcohol; polyacetals; ABS resins; ethylene vinyl acetate (EVA); polyesters such as polyethylene terephthalate and polybutylene terephthalate; polycarbonate; polyvinyl chloride; polyvinylidene chloride; polyvinylidene fluoride; polyether ether ketone (PEEK); polyphenylene oxide; styrene-acrylonitrile; polystyrene; polyester elastomers, polyurethane elastomers; polyacrylonitrile; as well as copolymers and blends of the foregoing, etc. As with the thermosetting resin particles, the heat retentive, solid additive, e.g., the antimicrobial agent, may be applied to the neat resin particle or to particles of a compounded resin composition: the latter typically including stabilizers, fillers, colorants, etc.

The type and size of the polymer particles is dependent upon the specific application to which the treated particles are to be used. For example, in water filtration applications, the treated particles may be on the order of 0.8 mm to 4 mm or more in loose fill applications or, on the order of 30 microns to 800 microns in the case of sintered, porous water filter media, as in Yao (U.S. Pat. No. 6,551,608) or Patil (U.S. Pat. No. 6,540,916). Similarly, powder coating compositions will typically have polymer particles on the order of 5 microns to 200 microns, more typically from 20 to 120 microns. Alternatively, for molding compositions, especially compression molding compositions, and masterbatch applications, the polymer particles will tend to have particle sizes on the order of 1 mm to 5 mm or more: particle size referring to the relative diameter in the case of spherical or spheroid particles or the highest aspect of the particle in the case of polymer pellets.

The present invention is applicable to most any solid, heat absorbing additive or material in particle form provided that the composition and mass, including size, of the particle is capable of being heated to a temperature at or above, preferably above, that at which the polymer to which it is to be bonded "begins to manifest adherent properties" and is capable of retaining a sufficient amount of that heat or heat energy until the bond is formed or, as appropriate, the conditions for forming the bond are established, i.e., the polymer at the interface of the additive and the polymer particle is heated to the temperature at which it manifests adherent properties. Certainly, the solid particle must be of a material or composition that is able to withstand the elevated temperatures required for effecting the bond.

Although there is essentially no limit on the additive materials that may be used, provided they meet the aforementioned limitations, the present invention is especially suited for use with inorganic solid particle materials. In particular, the present invention may be employed in adhering colorants, inorganic viscosity modifiers, fillers, flame retardants, catalysts, antimicrobial agents, fungicides, herbicides, insecticides, sequestering agents, blowing agents, EMI/RFI shielding additives and the like, especially antimicrobial agents, to polymer carrier particles. Such additives include any number of inorganic materials, especially, metal and metal ion containing materials, including metal oxides, metal salts, and the like. Those skilled in the art, having the benefit of the teachings of this specification, will readily realize other specific additives for which this inventive process is applicable. All such additives are well known and widely available and, as new additives are developed, their suitability for use herein will also be readily apparent. Furthermore, each will be used in their conventional amounts consistent with the objectives to be attained by their use. However, as noted below, surprisingly, certain additives may be employed in amounts less than conventionally used when compounded into the polymer or prepolymer of the powder coating composition while maintaining the same or even improved performance.

The process of the present invention is especially of benefit with those materials, especially polymer additives, a) that are co-reactive with a component, by-product or contaminant of the prepolymer and/or polymer particle, particularly under the extreme conditions of melt blending, b) that adversely affect the melt flow or physical properties of the polymer melt, or c) whose performance or purpose is adversely affected by its incorporation into the polymer matrix or by the process of its incorporation/association with the polymer matrix. In the case of co-reactive materials, the processing conditions of the present invention are generally less severe than those of melt blending: thus, it may be that the conditions are not conducive to manifestation of co-reactivity. Where co-reactivity is still possible, the extent of the same is limited to the interface between the polymer particle and the solid additive particle.

In following, many additives, especially inorganic additives like the flame retardant antimony oxide, tend to modify the melt flow characteristics of polymers into which they are incorporated. Thus, when the masterbatch material is added to a polymer melt, it oftentimes occurs that the molten masterbatch polymer has a higher viscosity than the melt into which it is added or being added. This difference in viscosity makes it more difficult to homogeneously disperse the one in the other. On the other hand, when the masterbatch is prepared in accordance with the present invention, the masterbatch viscosity is not affected by the presence of the thickening agent. Instead, the manifestation of viscosity modification will appear in the masterbatch polymer and the polymer melt into which it is incorporated at essentially the same time. As discussed above, by bonding, rather than incorporating, these additives to the polymer particles, the melt flow characteristics are not manifested until those particles are melt blended with another polymer particle.

Finally, decorative additives as well as functional additives, including, for example, conductive particles for EMI/RFI shielding and/or for dissipating electrostatic buildup as well as antimicrobial additives, especially inorganic antimicrobial additives, as well as other bioactive agents, such as fungicides, herbicides, etc., may not be as efficacious and/or may require much higher loadings (and added costs therefore) of the additives when incorporated throughout the matrix of the polymer when the only, or preferred or optimal, need is for the additive to be present at the surface of the polymer in its final end-use application. For example, ion-exchange type antimicrobial agents rely upon water transport as a means for the therein containing antimicrobial metal ions to release and provide their antimicrobial effect. When such materials are incorporated into a hydrophobic or poorly hydrophobic polymer, the antimicrobial agent within the matrix of the polymer is not available since water cannot reach it. Thus, when the antimicrobial agent is homogeneously incorporated into a polymer material, only a small portion of that material is present at the surface of the polymer. Thus, the greater proportion of antimicrobial agent is entombed within and unavailable or essentially unavailable to provide any bioefficacy. In contrast, in accordance with the present invention, all of the antimicrobial agent is available since it is all at the surface.

Depending upon the end-use application to which the coated particles of the present invention are applied, only a portion of the additive material may be available, but still, it is much higher than with those compositions wherein the additive is homogeneously incorporated into the polymer particle. For example, when the coated particles of the present invention are employed in compression molding or similar processes, the polymer particles will fuse together, entombing that antimicrobial agent on the surfaces that fuse; however, that which is on the exposed outer surface of the particles will remain and the melt will flow beneath it. Thus, upon completion of the compression molding and subsequent cooling cycle, the surface of the molded article will have a substantially uniform, highly concentrated level of the additive across its exposed surface: essentially only that quantity of additive on the unexposed surface of the polymer particles is lost.

Generally speaking, the heat absorbing, solid particles to be bonded to the polymer particles will be but a fraction of the size of the polymer particles to which they are to be bonded. Typically, they will be less than $1/10^{th}$ the size of the polymer particle, more likely less than $1/20^{th}$ the size, and, in the case of granular or pelletized polymer compositions for masterbatch, compression molding, or other molding applications, less than $1/50^{th}$, preferable less than $1/100^{th}$, the size of the polymer particles. The smallest size of additive particles capable of use in the present invention is dependent largely upon the heat absorbing characteristics of the given solid particles. Certainly, if they are so small as to be unable to absorb and retain sufficient heat to enable the bonding, they are not suitable for use in the practice of the present invention. Obviously, this will vary from material to material depending upon the material itself, its density and heat absorptive characteristics. Typically, though, the smallest particle size for the solid additive will be on the order of about 10 nanometers, preferably at least 100 nanometers, most preferably no less than 1 micron.

As mentioned, the present invention is especially suited for use in physically bonding antimicrobial agents to polymer particles. Preferred antimicrobial agents are inorganic antimicrobial agents that comprise or contain an antimicrobial metal or metal ion. Examples of such metals or metal ions include silver, copper, zinc, tin, gold, mercury, lead, iron, cobalt, nickel, manganese, arsenic, antimony, bismuth, barium, cadmium, chromium and thallium. Metals and metal ions of silver, copper, zinc, and gold are preferred because they are considered safe for in vivo use. Silver ions are more preferred due to the fact that they have the highest ratio of efficacy to toxicity, i.e., high efficacy to low toxicity; though combinations of silver and copper have recently been shown to have improved efficacy and/or color stability as compared to silver alone.

The antimicrobial agent can be in the form of simple salts or organometallic compounds of the antimicrobial metals such as the oxide, sulfide, chloride, bromide, carbonate, nitrate, phosphate, dihydrogen phosphate, sulfate, oxalate, acetate, benzoate, thiosulfate and the like. Specific examples include silver nitrate, cupric oxide, zinc acetate and zinc oxide. More recent attention has focused on the organometallic compounds derived from silver and various carboxylic acids, especially citric acid, acetic acid and the like, including silver citrate, silver dihydrogen citrate, tri-silver citrate and the like. Especially preferred are the silver citrates prepared though electrolysis as shown in Arata et. al., (U.S. Pat. No. 6,197,814, U.S. Pat. No. 6,583,176, and US 2005/0245605). Although simple salts and organometallic compounds are useful, they tend to be short lived due to quick and/or essentially uncontrolled dissolution. Thus, it may be desirable to employ metal particles, especially nanoparticles, of these metals, most especially nano-silver.

Alternatively, the antimicrobial agent may be in the form of a water soluble glass containing the antimicrobial agent or compound. Suitable antimicrobial water soluble glasses include those disclose in U.S. Pat. No. 5,470,585. By suitable adjustment of the glass composition, the dissolution rates in water can be controlled, thereby extending their longevity.

Preferably, the antimicrobial agent will be in the form of an ion-exchange type antimicrobial agent, alone or in combination with one or more other antimicrobial agents. Ion-exchange type antimicrobial agents are typically characterized as comprising a ceramic particle having ion-exchanged antimicrobial metal ions, i.e., the antimicrobial metal ions have been exchanged for (replaced) other non-antimicrobially effective ions in the ceramic particles. Additionally these materials may have some surface adsorbed or deposited metal; however, the predominant antimicrobial effect is as a result of the ion-exchanged antimicrobial metal ions.

Antimicrobial ceramic particles include, but are not limited to zeolites, hydroxyapatite, zirconium phosphates and other ion-exchange ceramics. These ceramic materials come in many forms and types, including natural and synthetic forms. For example, the broad term "zeolite" refers to aluminosilicates having a three dimensional skeletal structure that is represented by the formula: $XM_2/nO—Al_2O_3—YSiO_2-ZH_2O$ wherein M represents an ion-exchangeable ion, generally a monovalent or divalent metal ion; n represents the atomic valency of the (metal) ion; X and Y represent coefficients of metal oxide and silica respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange antimicrobial agents may incorporate most any antimicrobial metal ions, including those mentioned above. Most commonly, though silver ions or silver ions in combination with zinc and/or copper ions are used. The amount of antimicrobial metal ion is generally in the range of from about 0.1 to about 25 wt %, preferably from about 0.3 to about 20 wt %, most preferably from about 2 to about 10 wt %, based upon 100% total weight of ceramic carrier. Where other antimicrobial metal ions are present, the makeup will be from about 0.1 to about 15 wt % of silver ions and from about 0.1 to about 15 wt % of copper and/or zinc ions. These ion-exchange type antimicrobial agents may also have incorporated therein ion-exchanged ammonium ion for improved color stability. If present, the ammonium ion may be present at a level of up to about 20 wt % of the carrier; however, it is desirable to limit the content of ammonium ions to about 0.5 to about 2.5 wt %

All of the foregoing ion-exchange type antimicrobial agents are widely available and well known to those skilled in the art. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717 and 5,405,644. Antimicrobial zeolites containing antimicrobial metal ions are described in, e.g., U.S. Pat. Nos. 4,911,898; 4,911,899 and 4,938,958. Especially preferred ion-exchange antimicrobial agents are the antimicrobial zeolites available from AgION Technologies, Inc., of Wakefield, Mass., USA including, but not limited to product numbers AW10D (0.6% by weight of silver ion-exchanged in Type A zeolite particles having a mean average diameter of about 3μ), AG10N and LG10N (2.5% by weight of silver ion-exchanged in Type A zeolite particles having a mean average diameter of about 3μ and 10μ, respectively); AJ10D (2.5% silver, 14% by weight zinc, and between 0.5% and 2.5% by weight ammonium ion-exchanged therein in Type A zeolite having a mean average diameter of about 3μ); AK10D (5.0% by weight of silver ion-exchanged in Type A zeolite particles having a mean average diameter of about 3μ) and AC10D (6.0% by weight of copper and 3.5% by weight silver ion-exchanged in Type A zeolite particles having a mean average diameter of about 3μ).

Again, while the focus of the discussion herein has been made with respect to antimicrobial agents, the process of the present invention is in no way limited thereto. For example, as mentioned above, the invention is equally applicable to the other bioactive agents, especially those used in agriculture and horticulture, including fungicides and herbicides. Such bioactive agents overlap to a considerable extent with the aforementioned antimicrobial agents, particularly with respect to the metal containing fungicides, especially those based on copper and/or zinc. Again, all such materials are well known in the art. The amount by which each such additive is to be used in the practice of the present invention is consistent with and typical of their use in general. However, as noted, where the additive is such that its availability or efficacy is adversely affected by the incorporation of the same within the bulk of a polymer matrix, it is possible to use the same or lower levels while maintaining the same degree of efficacy as compared to masterbatch particles and the like where it is homogeneously incorporated into the polymer particle itself.

In accordance with the present invention, the thermosetting or thermoplastic polymer or prepolymer particles and the particles of the heat retentive/absorptive additive or material to be combined therewith are to be heated to two different temperatures. Specifically, the polymer or resin particles are heated to a temperature below that at which the surface of the particles begins to become tacky or manifest adherent properties. Preferably, the prepolymer and polymer particles are heated to at least their Vicat temperature but less than, preferably 2° C. to 5° C. less than, the temperature at which they begin to become tacky or manifest adherent properties.

The particles of the solid, heat absorbing materials, on the other hand, are heated to a temperature that is sufficiently higher than that of the prepolymer or polymer particles, based on its physical, heat absorptive, and heat transfer properties, so that when the two are in intimate contact with one another, preferably in forced contact, the heat transfer from the particles of the solid, heat absorbing material to the prepolymer or polymer particle at the point of contact is sufficient to cause the latter to become tacky or manifest adherent properties, thereby adhesively or fixedly binding the additive particles to the surface or within the surface layer of the prepolymer or polymer particles. Typically, the particles of the solid, heat absorbing material will be heated to a temperature that is at least about 10° C., preferably at least about 20° C., most preferably at least 50° C., above the temperature at which the prepolymer or polymer begins to become tacky or manifest adherent properties.

Of course the actual temperature to which the solid heat absorbing additive particles are to be raised will depend upon a number of different factors and variables including the temperature differential between the temperature at which the surface layer of the prepolymer or polymer particles begin to become tacky or manifest adherent properties and the actual temperature to which they are raised as well as the mass, the shape or geometry (especially surface area to mass ratio), the heat absorptive properties, and the heat transfer or heat loss characteristics of the solid heat absorbing additive material. For example, with respect to the latter, particles of large surface area to mass (i.e., one in a flake or fibrous form) will lose heat much more quickly and, therefore, may necessitate their heating to a higher temperature than may be necessary for a article of the same material and mass but a smaller surface area (e.g. a spherical or spheroid form). Similarly, additive particles of larger mass but the same composition will retain heat better than those of smaller mass and, thus, have more heat energy to transfer to the polymer particle to create the bond. Further, density and heat absorptive characteristics of composition of the additive particles will also vary. For example, particles of a metal such as steel would not require the same temperature elevation as similarly shaped and sized microparticles of a ceramic material. Here, the former may only require a temperature elevation of, for example, 5° C. to 10° C. above the temperature at which the polymer of the prepolymer or polymer particles begin to become tacky or manifest adherent properties, whereas the latter may require a temperature elevation of 40° C. to 50° C., or higher. Simple experimentation will enable one to select the proper temperature elevation needed for the chosen form and mass of the solid, heat absorbing microparticle material.

Bonding of the solid heat absorbing additive particles to the polymer or resin particles occurs as a result of a heat transfer from the former to the latter. Specifically, when the solid, heated additive particle comes into contact with the polymer or prepolymer particle, the monolayer, or at least a portion thereof, of polymer or prepolymer at the interface of the additive particle and the polymer or prepolymer material is heated to a temperature at or above that at which it becomes tacky or begins to manifest adhesive characteristics whereby the microparticle becomes bonded or adhered to the surface of the polymer or prepolymer particle. Alternatively, the heat transfer may be sufficient so that the surface monolayer of the polymer or prepolymer particle, or at least a portion thereof, is sufficiently softened whereby the additive particle becomes embedded in the softened monolayer, with or without true adhesion.

The process of the present invention may be employed in a batch type operation or in a continuous operation. The batch processing is especially suited for those polymers having high glass transition or melt temperatures due to the higher temperature demands of the process. Even so, with proper configuration of the apparatus, continuous processing is also possible.

In batch processing pre-determined quantities of the two components are heated to the appropriate temperatures and mixed together in a mixing vessel that is preferably configured to provide continuous heating and intimate mixing or blending of the two components. For example, the vessel is preferably maintained at or near the same temperature as that to which the polymer material is elevated. By maintaining the mixing vessel and the contents therein at an elevated temperature, one prevents the loss of too much heat from the additive particles to the atmosphere and, consequently, the failure of the same to bond to the polymer particles. Additionally, it is to be understood that somewhat higher mixing vessel temperatures could be used, especially where the heated prepolymer and/or polymer particles are added to the heated additive particles or where both are added gradually, with intermixing upon addition, into a third vessel, since the microparticles will coat the polymer particles and prevent substantial bonding of the polymer particles to the vessel walls and/or mixer components from occurring.

The materials in the mixing vessel will preferably be subjected to continuous mixing, agitation or tumbling. A stir means or auger-like means may be employed to provide continuous mixing or agitation. Alternatively, a mixer vessel which rotates, with or without projections, especially spiraling or thread-like projections, on the inner surface of the walls of vessels extending into the inner volume of the vessel, may be used for providing continual tumbling, much like a cement mixer. Mixing of the two components will ensure good dispersion of the one in and about the other so as to allow for a more even coating of the polymer particles with the solid additive particles: similar, if you will, to the coating of granulated sugar with powdered cinnamon.

For optimizing the throughput of the batch processing, it is preferable to heat the two components and combine the same in a third mixing vessel. In this manner, the components for the next process batch may be heated as the components of the present batch are being mixed. However, it is also contemplated that the mixing may occur in the vessel or chamber in which one of the two components is heated. Preferably, in this embodiment, the heated additive particles are gradually added to the vessel or chamber containing the heated polymer and/or prepolymer particles with constant mixing, agitation or tumbling so as to more evenly disperse the former over the latter; again, thereby providing more uniform coverage.

In yet another embodiment of the batch processing, the two components may be intimately mixed prior to or concurrent with heating and the mixture heated using microwave energy, induction heating (e.g., electromagnetic energy), or another suitable means which selectively and/or preferentially heats the additive particles as opposed to the polymer and/or prepolymer particles. For example, the mixture may be subjected to microwave energy wherein the compositional make-up of the solid additive particles is such that it absorbs the microwave energy faster and/or more efficiently than the polymer particles thereby elevating them above the temperature at which the prepolymer or polymer "begins to manifest adherent properties" before the polymer particles themselves reach their glass transition temperature or melt temperature, as appropriate. This method may be more energy efficient since one is not reliant upon conductive heating which oftentimes requires that the mixing vessels and associated equipment/components are also heated.

As noted, the present process is also capable of continuous operation. Here, for example, two feeder inlets supply constant flows of the heated polymer or resin particles and the heated heat absorbing additive particles to a mixing chamber, preferably heated, where the two are brought into intimate contact with one another and then exit from the mixing chamber through an outlet means. Intimate mixing of the two components may occur as a result of the intersecting of the flow streams and/or the cascading and tumbling thereof as they fall in the mixing chamber and progress into or on, as appropriate, the exit means. For example, the mixing chamber may have a series of cascading tilted shelves that cause the mixture to cascade back and forth as the materials fall through the mixing chamber to a catch basin, which then captures the mixture and passes it out of the mixing chamber. Alternatively, the mixing chamber may comprise a mixing or stir means or an auger-like means for mixing the components as they pass through the mixing chamber: passage through the mixing chamber being facilitated by a conveyance means that moves the mixture towards the exit. The conveyance means may be a belt or an auger-like device: the latter also providing mixing. Alternatively, the mixing chamber may rotate and have one or more screw-like or thread-like elements on the inner surface thereof that increases the mixing and progression of the materials through the mixing chamber. In yet another embodiment, the rotating mixing chamber may be titled with a series of shelves, circular projections or reverse screw-like or thread-like projections that impeded the movement of the particles from the top of the chamber to the bottom thereof such that progression occurs as a result of the spillover of the particles from one projection to the next.

As with the batch apparatus, the mixing chamber and/or elements thereof are preferably maintained at an elevated temperature so as to preclude too much heat loss from the microparticles before intimate mixing and bonding is attained with the polymer particles. Absent a configuration that ensures mixing of the two components before the polymer particles come into contact with the surface and/or elements of the mixing chamber, the temperature of the mixing chamber is preferably maintained below that temperature at which the polymer particles being to manifest adhesive characteristics. Otherwise, the surfaces should be composed of or be treated with a material to which the prepolymer and/or polymer particles will not adhere.

Generally speaking, any suitable heating means may be employed, for example heating may be by convection, conduction, induction, or by irradiation, including IR or, as noted above, microwave. Conductive heating is most common. In batch processing the walls of the vessels are heated. In continuous processing, the vessels or chambers which hold the materials before they are fed to the mixing chamber and/or the conduits themselves which transport the particles to the mixing chamber may have heated surfaces.

As mentioned above, the mixing vessel or chamber is preferably heating during the mixing step. Although lower temperatures are possible, it is preferable that the temperature of the mixing chamber be no less than, and more preferably at least 5° C. to 10° C. higher than, the Vicat temperature of the prepolymer and/or polymer particles, but less than, preferably at least 2° C. to 5° C. less than the temperature at which the prepolymer or polymer begins to become tacky or manifest adherent properties. By maintaining an elevated temperature within the mixing chamber or vessel, one minimizes concern for heat loss to the environment or surfaces of the mixing vessel or chamber. Obviously, it is a necessary objective of the process of the present invention to maintain sufficient absorbed heat in the components during the mixing step so as to ensure that the heat loss or, more appropriately, heat transfer upon contact of the additive particle and the prepolymer and/or polymer particle is sufficient to cause the prepolymer or polymer composition to begin to manifest adherent properties so as to created a tack or pre-bond and then continue to lose heat to form a formal bond: one that is not broken under the continued mixing conditions. In the preferred embodiments, the heat of the particles will be sufficient to melt or liquefy the polymer at the additive/polymer particle interface with the concurrent transfer/loss of heat so that the prepolymer or polymer material re-solidifies.

Optionally, the coated polymer particles upon exiting the mixing vessel of the batch processing apparatus or the mixing chamber of the continuous processing apparatus will be subjected to a screening so as to separate the free additive microparticles from the coated particles. The free additive microparticles may then be re-used in a subsequent coating process.

The process of the present invention has several benefits over the prior art methods. As discussed at length above, in certain circumstances, the present process allows one to prepare masterbatches of polymer additives that were not previously possible or, if possible, resulted in a less than desirable outcome. Similarly, for those additives that are functionally inactive when entombed, it allows one to avoid entombment or certainly significantly reduce the degree of entombment: thus, enabling one to achieve a higher degree of performance of the additive with the use of less additive.

Secondly, it avoids or significantly reduces agglomeration of the polymer or prepolymer particles as is oftentimes found with prior art fusion bonding methods. In these methods all the components are heated at the same time and to the same temperature. Consequently, there is a high tendency for the heated and now tacky polymer particles to bond to one another, not just the additive particles. Thus, it oftentimes becomes necessary to isolate and process by grinding the resultant agglomerations in order to break up the agglomerations and make the coated materials suitable for their intended end use. While some agglomeration is possible in the practice of the present invention, unlike the polymer-to-polymer particle agglomeration of the fusion bonding method, any agglomeration found with the present invention is likely to be as a result of the additive particles bridging the polymer particles. Such bonds are likely to be markedly weaker than with the polymer-to-polymer bonds and, thus, readily reversed with minimal effort.

Figure 1:
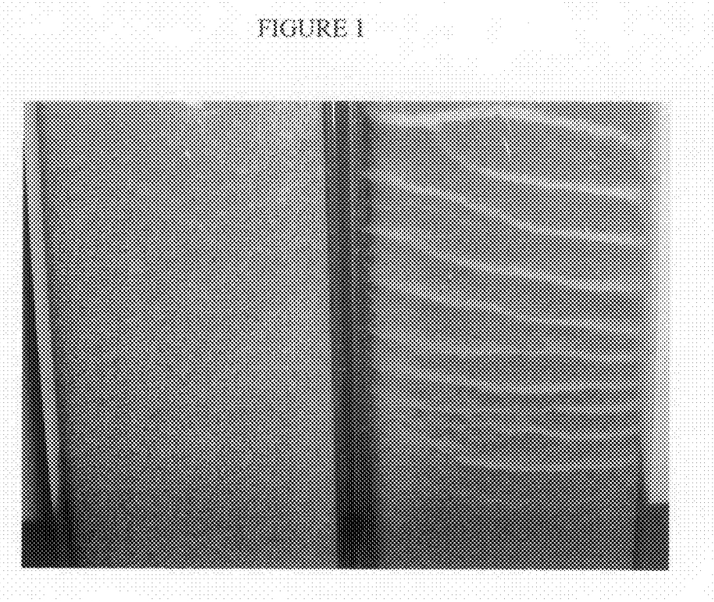
FIG. 1 is a drawing depicting the inventive composition and a comparative composition following tab vibration for 5 minutes.
Figure 2:
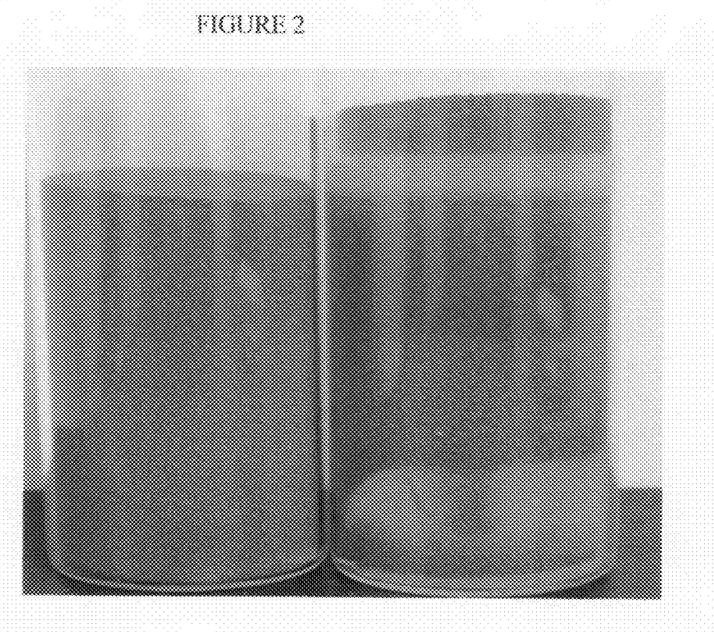
FIG. 2 is a drawing depicting the compositions of FIG. 1 following tap vibration for 3 hour.

Third, while many of the foregoing problems of the prior art methods may be avoided by use of a dry blending method, this method also has problems not associated with the present process. Specifically, the components have a tendency to separate and/or settle out, whereas with the coated particles of the present invention, a volume of the coated particles will maintain a relatively uniform concentration of the additive. This difference is clearly shown in FIGS. 1 and 2. Here two identical formulations were prepared each comprising about 91% by weight of Plastcoat NG10 polyethylene powder coating composition (95% less than 300μ particle size, 80° C. Vicat temperature and 107° C. melting point) from Plastcoat of Cleveland, Ohio, and about 9% by weight of AgION AJ10D silver zeolite antimicrobial agent (average particle size 3μ) from AgION Technologies of Wakefield, Mass. The dry blended composition, shown in the bottles on the left, was made by simply intimately mixing the two constituents until a substantially homogenous mixture was attained. The coated particles in accordance with the present invention, shown in the bottles on the right, were made by heating the silver zeolite at 300° C. for 60 minutes and the polyethylene powder at 100° C. for 60 minutes. The heated zeolite material was then combined with and mixed with the polyethylene powder to coat the latter with the former. A quantity of each composition was placed in a glass vial and the vials subjected to tapping using a sieve tapper. FIG. 1 shows the extent of separation following just five minutes of tapping. FIG. 2 shows the same compositions that have been shaken with the sieve tapper for 300 minutes.

Clearly, one can see that unless one subjected the dry blended materials to remixing immediately prior to use, a series of samples taken from the container will show a wide variation in additive concentration: in this case, aliquots of low and high silver content. Obviously, the performance or efficacy of the additive in products made from or treated with the dry blended particles will vary widely from one product to another as well as across the surface of a given product. Additionally, depending upon the nature of and concentration of the additive material, its presence in high concentrations may adversely affect the appearance and/or physical properties of the polymer and/or articles into which the dry blend is incorporated or to which it is applied. Conversely, a series of samples taken from the composition made in accordance with the present invention will show substantially uniform silver content from one sample to the other. Such consistency and stability will also manifest in articles of manufacture made from or treated with such materials.

Although the present invention has been described with respect to the specific embodiments mentioned above, it should be appreciated that other embodiments utilizing the concepts of the present invention are possible without departing from the scope of the invention. Thus, the present invention is defined by the claimed elements and any and all modifications, variations, or equivalents that fall within the spirit and scope of the underlying principles set forth herein.

We claim:

1. A method of fixedly coating (a) particles of a solid, heat absorbing material on the surface of (b) prepolymer and/or polymer particles, individually and collectively, the polymer particles, said method comprising i) heating the polymer particles to a temperature below that at which the surface of the particles begins to become tacky or manifest adherent properties, (ii) heating the particles of the solid, heat absorbing material to a temperature at or above the temperature at which the prepolymer or polymer of the polymer particles becomes tacky or begins to manifest adherent properties, (iii) bringing the two types of particles into contact with each other prior to, concurrent with or following the heating thereof, and (iv) allowing the particles of the solid, heat absorbing material to become fixed to the surface of the polymer particles as a result, in whole or in part, of the transfer of heat energy from the higher temperature heat absorbing particles to the surface of the polymer particles at their point of contact.

2. The method of claim 1 wherein the the heat transfer from the particles of the heat absorbing material to the polymer particles at the point of contact causes the latter, at the point of contact, to become tacky or manifest adherent properties, other than merely softening of the polymer or prepolymer material, thereby fixedly binding the particles of the heat absorbing material to the surface or within the surface layer of the polymer particles.

3. The method of claim 1 further comprising the step of intimately mixing the polymer particles and the particles of the solid, heat absorbing material, wherein the particles of the solid, heat absorbing material are heated to a temperature that is higher than that of the polymer particles so that when the two are in intimate contact with one another the heat transfer from the particles of the heat absorbing material to the polymer particles at the point of contact causes the latter, at the point of contact, to soften whereby the pressure of mixing the two together causes the former to become fixedly embedded in the surface of the latter.

4. The method of claim 1 wherein the polymer particles and the particles of the heat absorbing material are heated individually and subsequently combined.

5. The method of claim 1 wherein the polymer particles and the particles of the heat absorbing material are admixed and the admixture heated using a heating means that is selective for or preferential to the particles of the heat absorbing material.

6. The method of claim 1 wherein the polymer particles are heated to or within five degrees centigrade of their Vicat temperature and the particles of the heat absorbing material are heated to a temperature at least 10° C. higher than the Vicat temperature of the polymer particles.

7. The method of claim 1 wherein the polymer particles are heated to a temperature that is above the Vicat temperature and at least 2° C. lower than the temperature at which the polymer or prepolymer begins to manifest adhesive characteristics.

8. The method of claim 7 wherein the particles of the heat absorbing material are heated to a temperature that is at least 20° C. higher than the temperature at which the polymer particles begin to manifest adhesive characteristics.

9. The method of claim 7 wherein the particles of the heat absorbing material are heated to a temperature that is at least 50° C. higher than the temperature at which the polymer particles begin to manifest adhesive characteristics.

10. The method of claim 7 wherein the polymer particles are heated to a temperature that is at least 5° C. lower than the temperature at which the polymer or prepolymer begins to manifest adhesive characteristics.

11. The method of claim 1 wherein the heat absorbing material is a colorant, inorganic viscosity modifier, filler, flame retardant, catalyst, antimicrobial agent, fungicide, herbicide, insecticide, sequestering agent, blowing agent, granualated activated carbon, or an EMI/RFI shielding additive.

12. The method of claim 1 wherein the particles of the heat absorbing material are no more than $1/10^{th}$ the size of the polymer particles.

13. The method of claim 1 wherein the average particle size of the heat absorbing material is no more than $1/20^{th}$ that of the polymer particles.

* * * * *